United States Patent [19]

Sekimoto et al.

[11] Patent Number: 5,204,425

[45] Date of Patent: Apr. 20, 1993

[54] POLYALICYCLIC POLYACRYLIC ACID ESTER DERIVATIVES

[75] Inventors: Kenichi Sekimoto, Machido; Noriaki Oshima, Ebina; Yousuke Takahashi; Toru Seita, both of Atsugi, all of Japan

[73] Assignee: Tosoh Corporation, Shin-nanyo, Japan

[21] Appl. No.: 460,114

[22] PCT Filed: Oct. 12, 1989

[86] PCT No.: PCT/JP89/01048

§ 371 Date: May 14, 1990

§ 102(e) Date: May 14, 1990

[87] PCT Pub. No.: WO90/03987

PCT Pub. Date: Apr. 19, 1990

[30] Foreign Application Priority Data

Oct. 12, 1988 [JP] Japan ................. 63-254858
Mar. 15, 1989 [JP] Japan ................. 1-60693
Jul. 5, 1989 [JP] Japan ................. 1-171877

[51] Int. Cl.$^5$ ............................... C08F 24/00
[52] U.S. Cl. ........................................ 526/268
[58] Field of Search .......................... 526/268

[56] References Cited

U.S. PATENT DOCUMENTS 4,138,300  2/1979  Kaetsu et al. ............... 522/5
5,043,366  8/1991  Isozaki ........................ 526/268

FOREIGN PATENT DOCUMENTS 51-125491  11/1976  Japan .
02242820  9/1990  Japan ................. 526/268

Primary Examiner—Joseph L. Schofer
Assistant Examiner—Alex H. Walker
Attorney, Agent, or Firm—Oblon, Spivak, McClelland, Maier & Neustadt

[57] ABSTRACT

A polyacrylic acid ester derivative having repeating units represented by the formula:

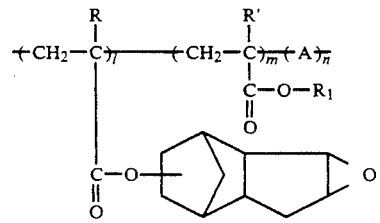

(wherein R and R' independently represent a hydrogen atom or a methyl group, $R_1$ represents a $C_1$-$C_4$ linear or branched alkyl group, A represents a structural unit derived from a group copolymerizable with an acrylic acid ester, and l, m and n are, respectively, from 0.04 to 1.0, from 0 to 0.96 and from 0 to 0.5 in this order, provided that their sum is 1, and when m is not higher than 0.2, n is a number of not higher than 0.01) and having a molecular weight of from about 5,000 to about 1,000,000, is capable of being molded, and is useful as an optical material.

10 Claims, 2 Drawing Sheets

POLYALICYCLIC POLYACRYLIC ACID ESTER DERIVATIVES

TECHNICAL FIELD

The present invention relates to polyalicyclic polyacrylic acid ester derivatives. This polymer resin composition is particularly useful as a resin for optical material to be used for optical lenses, digital audio disks, or optical memory disks.

BACKGROUND TECHNIQUE

Acrylic resins such as polymethyl methacrylate have been used for optical lenses, digital audio disks, optical memory disks, optical fibers, etc. by virtue of their properties such as transparency and strength (Japanese Unexamined Patent Publications No. 74701/1982 and No. 180906/1988. However, with conventional acrylic resins, drawbacks have been pointed out such that their glass transition temperature is low, and their water absorptivity is high. Various methods have been proposed to solve these problems. For example, Japanese Unexamined Patent Publications No. 151413/1987 and No. 72708/1988 and Japanese Examined Patent Publication No. 28419/1971 disclose methods intended to improve the heat resistance or to reduce the after absorptivity. However, these methods still have many problems with respect to e.g. the moldability and have not been practically used.

As opposed to such acrylic resins, epoxy resins have been known as resins having high heat resistance. However, epoxy resins have a problem with respect to e.g. the molding time, although they are excellent in the optical properties such as transparency and optical anisotropy like the acrylic resins. In the bulk reaction by photocuring by means of ultraviolet rays, a problem has been pointed out such that it is difficult to attain a high molecular weight or three dimensional crosslinking.

SUMMARY OF THE INVENTION

Under the above described circumstances, the present inventors intend to provide a polymer resin composition having a high glass transition temperature and a small water absorptivity while maintaining the characteristics of the conventional methacrylic resins with respect to the transparency and strength and a shaped product of optical material formed from such polymer resin composition.

The present inventors have conducted extensive studies to solve the above problems. As a result, they have found that a derivative comprising, as a basic constituting component, a polyalicyclic acrylic acid ester derivative represented by the following formula (2):

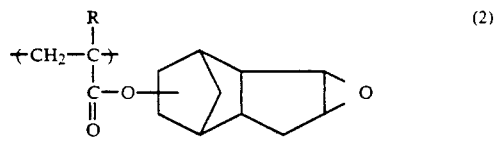

provides physical properties excellent in the optical uniformity, mechanical strength, heat resistance and water absorptivity, and it is possible to obtain a shaped product of optical material by using this derivative. Thus, the present invention has been accomplished.

Namely, the present invention provides a polyalicyclic polyacrylic acid ester derivative represented by the formula (1):

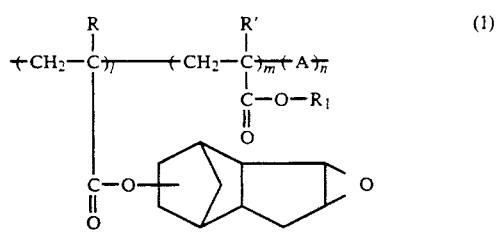

(wherein R and R' independently represent a hydrogen atom or a methyl group, $R_1$ represents a $C_1$-$C_4$ linear or branched alkyl group, A represents a structural unit derived from a group copolymerizable with an acrylic acid ester, and l, m and n are, respectively, from 0.04 to 1.0, from 0 to 0.96 and from 0 to 0.5 in this order, provided that their sum is 1, and when m is not higher than 0.2, n is a number of not higher than 0.01) and having a molecular weight of from about 5,000 to about 1,000,000. As an acrylic acid ester derivative, from which the structural unit A is derived, a monomer represented by the formula:

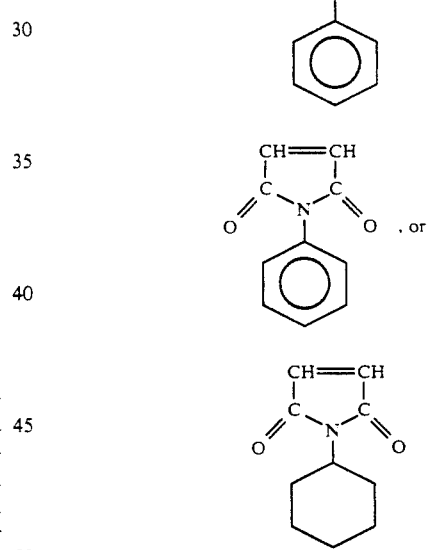

may be exemplified.

A polymer represented by the formula (3)

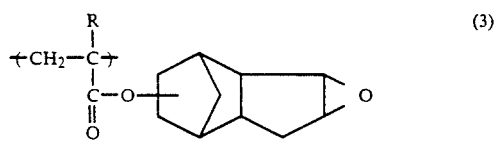

(wherein R is a hydrogen atom or a methyl group), wherein m and n are simultaneously 0 in the formula (1), has extremely high heat resistance, and its glass transition temperature is at least 200° C. This is desirable. On the other hand, the melting temperature is high, and when a resin composition containing this polymer is to be molded, a temperature substantially higher than those for other acrylic resins will be required.

On the other hand, a polymer wherein m is other than 0 and n is 0 in the formula (1), i.e. a polymer represented by the formula (4):

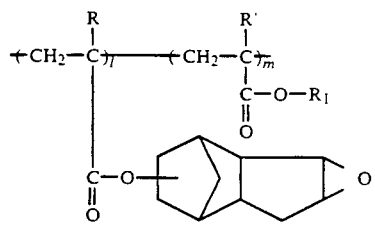 (4)

(wherein R and R' independently represent a hydrogen atom or a methyl group, and $R^1$ is a $C_1$-$C_4$ linear or branched alkyl group, and a polymer wherein both m and n are other than 0, particularly a copolymer represented by the formula (5), (6) or (7):

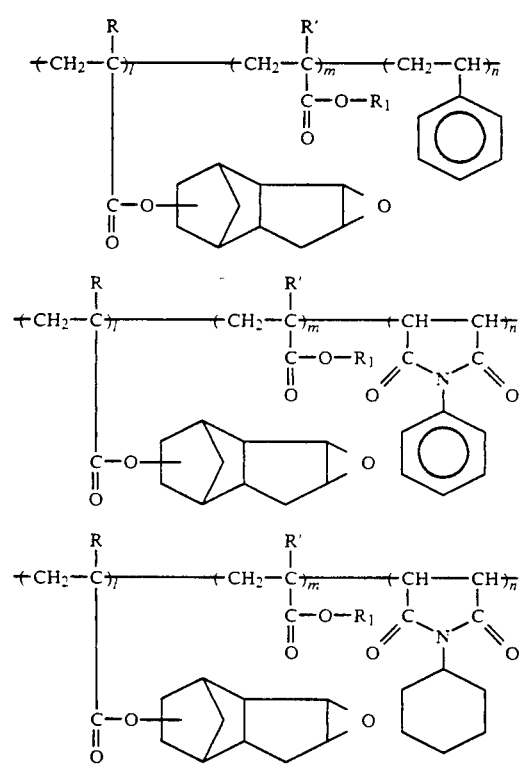

(wherein R and R' independently represent a hydrogen atom or a methyl group, and RI represents a $C_1$-$C_4$ linear or branched alkyl group) has different characteristics in their thermal properties.

For example, the copolymer of the formula (4) is capable of adjusting the glass transition temperature of the polymer of the formula (3) by its copolymerization ratio, and the copolymer of the formula (5) is rich particularly in the fluidity when melted. Further, the polymers of the formulas (6) and (7) are excellent particularly in the heat decomposition resistance.

The compound of the formula (2) useful for the production of the polyalicyclic polyacrylic acid ester derivative of the present invention, can be obtained by reacting 3,4-epoxyhydroxytricyclo[5.2.1.0$^{2,6}$]decane with acryloyl chloride or methacryloyl chloride in the presence of a base in an inert gas at a reaction temperature of from −50° to 100° C., preferably from 0° to 50° C., for a reaction time of from 0.5 to 30 hours, preferably from 1 to 10 hours. For the reaction, a solvent may be added, as the case requires. As the solvent to be used here, n-hexane, n-pentane, cyclohexane, benzene, toluene, xylene, trichloroethylene, tetrachloroethylene, chloroform, diethyl ether, tetrahydrofuran or diisopropyl ether may, for example, be mentioned. As the base, an alkali metal hydroxide such as sodium hydroxide or potassium hydroxide, an alkali metal hydride such as sodium hydride or potassium hydride, an alkali metal carbonate such as sodiumcarbonate or potassiumcarbonate, an alkali metal hydrogencarbonate such as sodium hydrogen carbonate or potassium hydrogen carbonate, or an amine such as pyridine, triethylamine or dimethylaminopyridine, may be used.

The monomer (2) synthesized as described above is polymerized alone or copolymerized with an acrylic monomer of the formula (8):

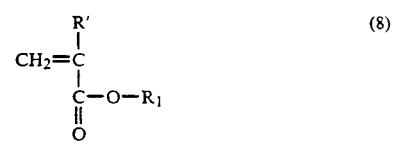 (8)

(wherein R' is a hydrogen atom or a methyl group, and $R_1$ is a $C_1$-$C_4$ linear or branched alkyl group) and a group copolymerizable with an acrylic acid ester, such as a monomer of the formula (9):

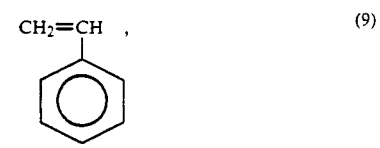 (9)

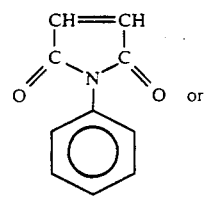 or

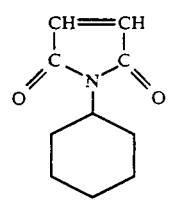

to obtain the desired polymer. The proportions of these monomers are from 0.04 to 1, from 0 to 0.96 and from 0 to 0.5 as the molar fractions of (2), (8) and (9), respectively, their sum is 1, and when the fraction of the formula (8) is at most 0.2, the fraction of the formula (9) is at most 0.01.

As the polymerization method, a usual radical polymerization method such as bulk polymerization, solution polymerization or suspension polymerization, may be employed.

As a polymerization initiator to be used at that time, for example, an organic peroxide such as benzoyl peroxide, diisopropyl peroxide, tert-butyl peroxy pivalate or lauroyl peroxide, an azo compound such as azo isobisbutyronitrile, as a photopolymerization initiator, a photosensitizer such as benzophenone, benzoinethyl ether, dibenzyl, acetophenone or anthraquinone, or a sulfur compound such as diphenyl sulfide or thiocarbamate, may be employed. The amount of the polymerization initiator is usually within a range of from 0.001 to 10 parts by weight, preferably from 0.01 to 10 parts by weight, per 100 parts by weight of the total monomers.

The polymerization temperature varies depending upon the type of the polymerization initiator, but is usually within a range of from 0° to 200° C., preferably from 50° to 120° C.

By the foregoing process, it is possible to obtain a copolymer having the above-mentioned repeating units (6) of the present invention. This polymer has a molecular weight of from about 5,000 to 1,000,000, preferably from 30,000 to about 500,000.

In the present invention, the polymer thus obtained, is molded by a common molding method for a polymer resin composition, such as injection molding, to form a shaped product of optical material. Further, during such molding, an antioxidant, an antistatic agent, etc. may be added as the case requires.

This shaped product may be able to provide the desired physical properties adequately and is practically useful by itself. However, for the purpose of further improving the heat resistance after the molding of the shaped product or improving the mechanical strength, it is possible to add a cross-linking agent to the polymer shown by the formula (3), (4), (5), (6) or (7) and form a three dimensionally cross-linked product by the action of light and/or heat.

This process is conducted by adding an epoxy curing catalyst, a curing agent or a curing accelerator to the polycyclic acrylic acid ester derivative obtained as described above.

As the photocurable catalyst, an onium salt compound such as a Lewis acid anion of a composite of a photocleaving-type silanol derivative and an aluminum chelate, may be mentioned. As the onium salt in the onium salt of a Lewis acid anion, an aromatic halonium salt such as a diaryl iodonium salt or a diaryl bromonium salt, an aromatic chalconium salt such as a triaryl sulfonium salt or a triaryl selenium salt, or a diazonium salt may be employed as the one which effects photocleavage effectively. As the Lewis acid, the one capable of forming a salt together with an onium ion, such as $ClO_4-$, $BF_4-$, $BF_6-$, $PF_6-$, $AsF_6-$ or $SbF_6-$, may be mentioned.

In the photocleaving-type silanol derivative-aluminum chelate composite compound, as the photoleaving-type silanol derivative, o-nitrobenzylsilyl ether, a trialkylmethanesilyl peroxide or the like which is obtained by modifying silanol with o-nitrobenzyl alcohol, a trialkylmethane hydroperoxide or the like, may be used. As the aluminum chelate, an aluminum-trisacetoacetic acid ester chelate such as aluminum-trisethylacetoacetate, an aluminum-tris-o-carbonylphenol chelate such as aluminumtrisalicylaldehydate, or aluminum-trisacetylacetone chelate, may be employed.

The amount of the photocuring catalyst is usually from 0.01 to 5 parts by weight, preferably from 0.01 to 1 part by weight, per 100 parts by weight of the polymer of the polyalicyclic acrylic acid ester derivative of the present invention. Further, in additive such as a photosensitizer or a stabilizer, may be used as the case requires. The light to be used for curing varies depending upon the curing catalyst, but it is usually from 180 to 700 nm, and ultraviolet rays are particularly effective. As the light source, a low pressure mercury lamp, a high pressure mercury lamp, a carbon arc lamp, a metal halide lamp, a hydrogen discharge tube, a tungsten filament lamp, a halogen lamp, a sodium dicharge tube, a neon discharge tube, a He—Ne laser or an Ar laser may, for example, be mentioned. The irradiation time is preferably from 1 second to 15 minutes.

As the curing agent to be used for heat curing, an aliphatic polyamine, an aromatic polyamine, an amine such as a secondary or tertiary amine, a fatty acid, a polyamide resin such as a condensation product of a fatty acid such as a dimer acid or trimer acid with an aliphatic polyamine, or an acid anhydride such as phthalic anhydride, tetrahydrophthalic anhydride, hexahydrophthalic anhydride, trimellitic anhdyride, pyromellitic anhydride, benzophenonetetracarboxylic anhydride, chlorendic anhydride, dodecylsuccinic anhydride, methyltetrahydrophthalic anhydride or methylendomethylenetetrahydrophthalic anhydride, or a complex of boron trifluoride with monoethylamine, piperidine, aniline, butyl amine or triethanol amine, may be mentioned. The curing agent is incorporated in an amount of from 5 to 200 parts by weight relative to 100 parts by weight of the epoxy prepolymer.

As the curing accelerator, a tertiary amine such as triethylene diamine, benzyldimethyl amine, triethanol amine, dimethylethanol amine, dimethylaminoethanol amine or tri(dimethylaminomethyl)phenol, an imidazole such as 2-methylimidazole, 2-phenyl imidazole, 2-phenyl-4-methylimidazole or 2-heptadecyl imidazole, an organic phosphine such as tributyl phosphine, methyldiphenyl phosphine, diphenyl phosphine, triphenyl phosphine or phenyl phosphine, or a tetraphenylboron salt such as tetraphenol phosphonium tetraphenylborate or 2-ethyl-4-methylimidazoltetraphenyl borate, may be mentioned. The curing accelerator is used in an amount of from 0.01 to 10 parts by weight, preferably from 0.05 to 5 parts by weight, relative to 100 pats by weight of the total amount of the polymer and the curing agent used.

The heat curing is conducted usually at a temperature of from 0° to 200° C., preferably from 20° to 130° C.

At the time of cross-linking and curing the resin of the present invention, an antioxidant, an antistatic agent, a ultraviolet absorber or a releasing agent may be added as the case requires.

It should be understood that the above syntheses and polymerization methods are given for the purpose of illustration, and the present invention is not limited to such specific methods. As a method for forming a three dimensional cross-linked product, the following method is also possible. Namely, a polymerization initiator is added to the monomer of the formula (2), and the polymerization reaction and the cross-linking reaction are simultaneously conducted by the action of light and/or heat. It has been found that also the resin obtainable by this method is excellent in the transparency, heat resistance, moisture resistance, mechanical strength and optical uniformity. In this method, a photocuring initiator, a heat curing initiator, a curing agent or a curing accelerator may be added to the compound of the formula (2), as the case requires, and the desired three dimensionally cross-linked resin shaped product is produced by a photocuring reaction or a heat curing reaction, or by a combination of both curing reactions.

As the photocuring initiator, the same onium salt compound of a Lewis anion or a composite of a photocleaving-type silanol derivative with an aluminum chelate as used for the cross-linking and curing of the polymers of the formulas (3), (4), (5), (6) and (7) may be used as the one reacting to the epoxy group of the compound of the formula (2). This photocuring initiator is used usually in an amount from 0.01 to 5 parts by weight, preferably from 0.01 to 1 part by weight, relative to 100 parts by weight of the monomer.

Further, as the photocuring initiator which acts on the vinyl bond in the acrylic acid ester in the formula (2), a photosensitizer such as benzopheone, benzoin ethyl ether, dibenzyl, acetophenone or anthraquinone, or a sulfur compound such as diphenyl sulfide or thiocarbamate, may be employed. This initiator is used in an amount within a range of from 0.001 to 10 parts by weight, preferably from 0.01 to 5 parts by weight, relative to 100 parts by weight of the compound of the formula (2).

For the light to be used for the curing, the same light source as used for the cross-linking and curing of the polymers of the formulas (3), (4), (5), (6) and (7), may be used. The irradiation time is preferably from 1 second to 15 minutes.

As the epoxy curing agent to be used for the heat curing, the same aliphatic polyamine, aromatic polyamine, an amine such as a secondary or tertiary amine, a fatty acid, a polyamide resin such as a condensation product of a fatty acid such as a dimer acid or trimer acid with an aliphatic polyamine, acid anhydride such as phthalic anhydride, tetrahydrophthalic anhydride, hexahydrophthalic anhydride, trimellitic anhydride, pyromellitic anhydride, benzophenone tetracarboxylic anhydride, chlorendic anhydride, dodecyl succinic anhydride, methyl tetrahydrophthalic anhydride or methylendotetrahydrophthalic anhydride, or a complex of boron trifluoride with monoethylamine, piperidine, aniline, butyl amine or triethanol amine, as used for the cross-linking and curing of the polymers of the formulas (3), (4), (5), (6) and (7), may be mentioned. The curing agent is incorporated in an amount of from 5 to 200 parts by weight, relative to 100 parts by weight of the compound of the formula (2). As a heat polymerization initiator which acts on the vinyl bond in the acrylic acid ester in the formula (2), an organic peroxide such as benzoyl peroxide, diisopropyl peroxide, tert-butyl peroxypivalate or lauroyl peroxide, or an azo compound such as azoisobisbutyronitrile, may, for example, be mentioned. The polymerization initiator is used in an amount within a range of from 0.01 to 10 parts by weight, preferably from 0.1 to 5 parts by weight, relative to 100 parts by weight of the compound of the formula (2). As a curing accelerator, the same curing accelerator as used for the cross-linking and curing of the polymers of the formulas (3), (4), (5), (6) and (7), may be used. The curing accelerator is used in an amount of from 0.01 to 10 parts by weight, preferably from 0.05 to 5 parts by weight, relative to 100 parts by weight of the monomer and the epoxy curing initiator.

At the time of curing the resin of the present invention, an antioxidant, an antistatic agent, a ultraviolet absorber, a photosensitizer, a stabilizer, a releasing agent, etc. may be added as the case requires.

Further, for the purpose of controlling the transparency, mechanical strength or heat resistance, a monomer radical copolymerizable with the monomer of the formula (2), such as methyl acrylate, methyl methacrylate, styrene, N-pehnylmaleimide or N-cyclohexylmaleimide, may be incorporated to the monomer (2) to obtain a curing composition.

The molding is conducted by a casting method under an anaerobic condition. The curing temperature is within a range of from 0° to 200° C. in a case where only a photocuring reaciaction is used, or within a range of from 50° to 200° C. in a case where a heat curing reaction is used.

By the foregoing process, a three dimensionally cross-linked product of an alicyclic acrylic acid ester of the present invention can be produced.

The three dimensionally cross-linked polymer composition of the present invention is composed of a polymer having repeating units of the formula (10):

(wherein R is a hydrogen atom or a methyl group).

The above-mentioned curing method is given for the purpose of illustration, and the present invention is not limited to such a specific method.

BEST MODE FOR CARRYING OUT THE PRESENT INVENTION

Now, the present invention will be described in further detail with reference to Examples. However, the present invention is by no means restricted to such specific Examples. Various physical properties obtained in these Examples, were measured by the following testing methods.

(1) Light transmittance: Light transmittance at 500 nm was measured by a spectrophotometer Double refraction: Measured at the portion of the shaped product having a diameter of 80 mm by a polarizing microscope equipped with a Senarmon compensator, manufactured by Nippon Kogaku K.K..

Heat distorsion temperature: Measured by a heat distorsion testing apparatus in accordance with ASTM D-648

(4) Hardness: Measured by a tensile strength testing apparatus in accordance with JIS K-6911

(5) Water absorptivity: Measured in accordance with ASTM

EXAMPLE 1

Figure 1:
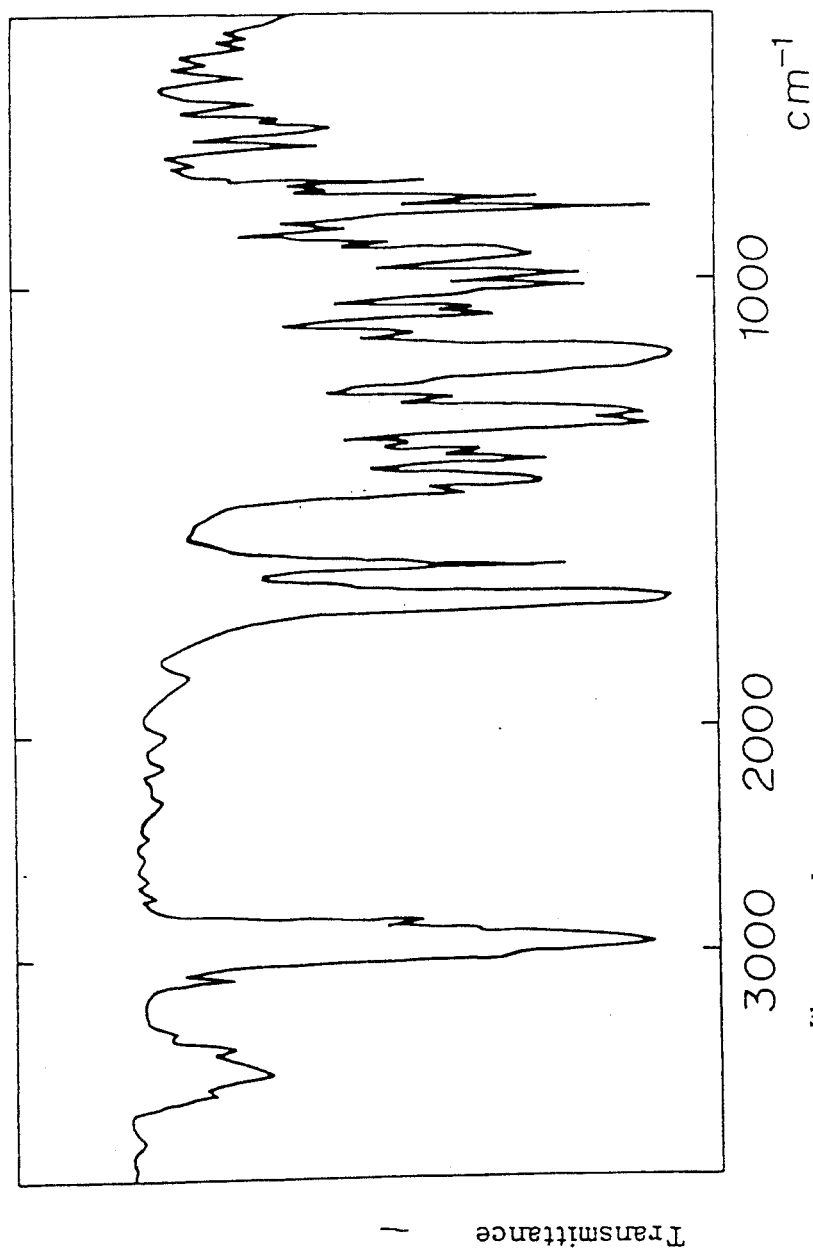
FIG. 1 is a chart showing the infrared absorption spectrum of the monomer of the polyalicyclic acrylic acid ester derivative of the present invention prepared in Example 1.

Into a 3 ml flask equipped with a dropping funnel, 116 g of 3,4-epoxyhydroxytricyclo[5.2.1.0$^{2.6}$]decane, 500 ml of ethyl ether and 200 g of sodium hydroxide were introduced and stirred under an argon atmosphere. Then, 250 ml of methacryloyl chloride was dropwise added thereto, and the mixture was reacted under stirring at 15° C for 3 hours. After completion of the reaction, the reaction mixture was washed 5 times with pure water. The organic layer was separated from the aqueous layer. Then, the solvent was distilled off from the organic layer under reduced pressure for concentration. Then, distillation under reduced pressure was conducted at 130° C. under a reduced pressure of 1 mmHg to obtain 195 g of 3,4-epoxymethacryloxyloxytricyclo[5.2.1.0$^{2.6}$]decane as the reaction product. The IR spectrum chart of the product is shown in FIG. 1.

EXAMPLE 2

195 g of 3,4-epoxymethacryloyloxytricyclo[5.2.1.0$^{2.6}$]decane obtained in Example 1 was dissolved to obtain a 18 wt% benzene solution. Then, 25 mg of azoisobisbutyronitrile was added thereto as a polymerization initiator. After evacuation, polymerization was conducted 75° C. for 5 hours.

After completion of the reaction, the product was poured into methanol to recover the desired polymer.

The polymer thus obtained was dissolved in tetrahydrofuran and then poured into methanol for purification. The white solid thus obtained was dried under vacuum at 40° C., and then the obtained amount was measured, whereby the amount was 117 g.

Figure 2:
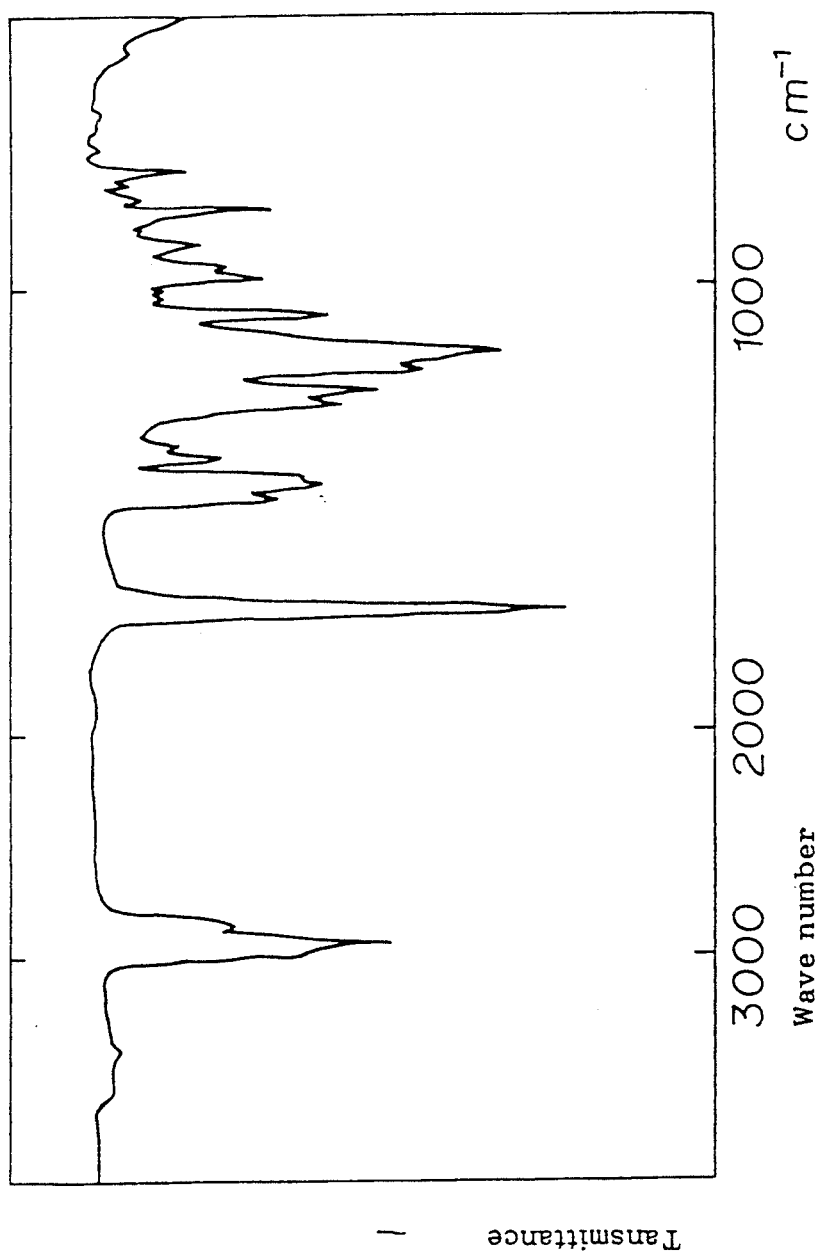
FIG. 2 is a chart showing the infrared absorption spectrum of the polymer of the polyalicyclic acrylic acid ester derivative of the present invention prepared in Example 2.

With respect to the polymer thus obtained, the GPC measurement was conducted, whereby the weight average molecular weight was 11.8×10$^4$ as calculated as polystyrene. Further, the IR spectrum chart of the product is shown in FIG. 2.

Further, the glass transition temperature of this polymer was measured by a differential thermal analysis and was found to be 213° C.

To 100 g of this polymer, 1 g of 4-phenylthiophenyl diphenylsulfoniumhexafluoroantimonate was added and mixed and then press-molded by means of a casting mold having a diameter of 120 mm and a thickness of 1.2 mm, followed by three dimensional cross-linking by irradiating ultraviolet rays (80 W/cm$^2$, distance: 20 cm) for 30 seconds.

With respect to the shaped product thus obtained, the light transmittance, double refraction, heat distorsion temperature, hardness and water absorptivity were measured. The results are shown in Table 1.

EXAMPLE 3

In the same manner as in Example 1, 3,4-epoxymethacryloyloxytricyclo[5.2.1.0$^{2.6}$]decane was synthesized. The obtained amount of the reaction product was 198 g. The obtained 3,4-epoxymethacryloyloxytricyclo[5.2.1.0$^{2.6}$]decane was dissolved to obtain a 15 wt% benzene solution, and then 36 mg of azoisobisbutyronitrile was added as a polymerization initiator. After evacuation, polymerization was conducted at 75° C. for 3.5 hours.

After completion of the reaction, the product was poured into methanol to recover the desired polymer.

The polymer thus obtained was dissolved in tetrahydrofuran and again poured into methanol for purification. The white solid thus obtained was dried under vacuum at 40° C., and then the obtained amount was measured, whereby the amount was 138 g.

With respect to the polymer thus obtained, the GPC measurement was conducted, whereby the weight average molecular weight was 8.4×10$^4$ as calculated as polystyrene.

To 100 g of the polymer thus obtained, 30 g of phthalic anhydride was added. This composition was press-molded in the same manner as in Example 2 and then maintained at 100° C. for 3 hours for three dimensional cross-linking. The physical properties of the shaped product thus obtained are shown in Table 1.

EXAMPLE 4

300 g of 3,4-epoxymethacryloyloxytricyclo[5.2.1.0$^{2.6}$]decane as a monomer obtained in the same manner as in Example 1 and 700 g of methyl methacrylate were mixed and dissolved to obtain 1,000 g of a benzene solution. To this benzene solution, 12 g of azoisobisbutyronitrile was added as a polymerization initiator. After evacuation, radical copolymerization was conducted under an argon atmosphere at 75° C. for 3 hours. After completion of the reaction, the product was poured into methanol to recover the desired polymer. The weight average molecular weight of the polymer thus obtained was 75,000 as calculated as polystyrene.

This polymer was injection-molded at 240° C. to obtain a shaped product having a diameter of 120 mm and a thickness of 1.2 mm. Then, the light transmittance, double refraction, heat distorsion temperature, hardness and water absorptivity were measured. The results are shown in Table 1.

EXAMPLE 5

200 g of 3,4-epoxymethacryloyloxytricyclo[5.2.1.0$^{2.6}$]decane as a monomer obtained in the same manner as in Example 1 and 800 g of methyl methacrylate were mixed and dissolved to obtain 1,000 g of a benzene solution. To this benzene solution, 12 g of azoisobisbutyronitrile was added as a polymerization initiator, and radical copolymerization was conducted in the same manner as in Example 2. After completion of the reaction, the product was poured into methanol to recover the desired polymer. The weight average molecular weight polymer thus obtained was 80,000 as calculated as polystyrene.

This polymer was injection-molded under the same condition as in Example 4, and the light transmittance, double refraction, heat distorsion temperature, hardness and water abosorptivity were measured. The results are shown in Table 1.

EXAMPLE 6

702 g of 3,4-epoxymethacryloyloxytricyclo[5.2.1.0$^{2.6}$]decane as a monomer obtained in the same manner as in Example 1, 600 g of methyl methacrylate and 104 g of styrene were mixed with 1,400 g of benzene. To this benzene solution, 14 g of azoisobisbutyronitrile was added as a polymerization initiator. After evacuation, radical copolymerization was conducted under an argon atmosphere at 75° C. for 3 hours. After completion of the reaction, the product was poured into methanol to recover the desired polymer. The weight average molecular weight of the polymer thus obtained was 92,000 as calculated as polystyrene.

This polymer was injection-molded at 240° C. to obtain a shaped product having a diameter of 120 mm and a thickness of 1.2 mm. Then, the light transmittance, double refraction, heat distorsion temperature, hardness and water absorptivity were measured. The results are shown in Table 1.

EXAMPLE 7

468 g of 3,4-epoxymethacryloyloxytricyclo[5.2.1.0$^{2.6}$]decane as a monomer obtained in the same manner as in Example 1, 700 g of methyl methacrylate and 177 g of N-phenylmaleimide were dissolved in 1,350 g of benzene. To this benzene solution, 12.7 g of azoisobisbutyronitrile was added as a polymerization initiator, and radical copolymerization was conducted for 5 hours in the same manner as in Example 2.

After completion of the reaction, the product was poured into methanol to recover the desired polymer. The weight average molecular weight of the polymer thereby obtained was 89,000 as calculated as polystyrene.

This polymer was injection-molded at 245° C. to obtain a shaped product having a diameter of 120 mm and a thickness of 1.2 mm. Then, the light transmittance, double refraction, heat distorsion temperature, hardness and water absorptivity were measured. The results are shown in Table 1.

EXAMPLE 8

468 g of 3,4-epoxymethacryloyloxytricyclo[5.2.1.0$^{2,6}$]decane as a monomer obtained in the same manner as in Example 1, 700 g of methyl methacrylate and 182 g of N-cyclohexylmaleimide were dissolved in 1,350 g of benzene. To this benzene solution, 13 g of azoisobisbutyronitrile was added as a polymerization initiator and radical copolymerization was conducted in the same manner as in Example 7.

After completion of the reaction, the product was poured into methanol to recover the desired polymer. The weight average molecular weight of the polymer thereby obtained was 87,000 as calculated as polystyrene.

This polymer was injection-molded at 245° C. to obtain a shaped product having a diameter of 120 mm and a thickness of 1.2 mm. Then, the light transmittance, double refraction, heat distorsion temperature, hardness and water absorptivity were measured. The results are shown in Table 1.

EXAMPLE 9

To 100 g of 3,4-epoxymethacryloyloxytricyclo[5.2.1.0$^{2,6}$]decane obtained in Example 1, 0.5 g of benzophenone and 1 g of 4-phenylthiophenyldiphenylsulfonium hexafluoroantimonate were added. This composition was subjected to evacuation under vacuum and then injected into a casting mold constituted by glass plates having a diameter of 120 mm and a spacer having a thickness of 1.2 mm, and ultraviolet rays (80 W/cm, distance: 20 cm) were irradiated by a metal halide lamp, whereby a cured shaped product was obtained in 10 minutes.

With respect to the disk-shaped product thus obtained, the water absorptivity, light transmittance, tensile strength, double refraction and heat distorsion temperature were measured. The results are shown in Table 1.

EXAMPLE 10

To 100 g of 3,4-epoxymethacryloyloxytricyclo[5.2.1.0$^{2,6}$]decane obtained in Example 1, 0.5 g of azoisobisbutyronitrile and 30 g of phthalic anhydride were added. This composition was subjected to evacuation under vacuum and injected into a casting mold constituted by glass plates having a diameter of 120 mm and a spacer having a thickness of 1.2 mm and heat-cured at 100° C., whereby a cured shaped product was obtained in 3 hours.

With respect to the disk-shaped product thus obtained, the water absorptivity, light transmittance, tensile strength, double refraction and heat distorsion temperature were measured. The results are shown in Table 1.

EXAMPLE 11

To 100 g of 3,4-epoxymethacryloyloxytricyclo[5.2.1.0$^{2,6}$]decane obtained in Example 1, 0.5 g of benzophenone, 1 g of 4-phenylthiophenyldiphenylsulfonium hexafluoroantimonate, 0.5 g of azoisobisbutyronitrile and phthalic anhydride were added. This composition was subjected to evacuation under vacuum and then injected into a casting mold constituted by glass plates having a diameter of 120 mm and a spacer having a thickness of 1.2 mm and irradiated with ultraviolet rays (80 W/cm, distance: 20 cm), by a metal halide lamp while maintaining the temperature at 100° C., whereby a cured shaped product was obtained in 1 minute.

A cured shaped product was withdrawn from the casting mold, and the water absorptivity, light transmittance, tensile strength, double refraction and heat distorsion temperature were measured. The results are shown in Table 1.

TABLE 1

| Example No. | Light transmittance (%) | Double refraction (nm) | Heat distorsion temp. (°C.) | Pencil hardness | Water absorptivity (%) |
|---|---|---|---|---|---|
| 2 | 91 | 5 | 178 | 3H | 0.12 |
| 3 | 91 | 4 | 175 | 3H | 0.14 |
| 4 | 90 | 5 | 141 | 3H | 0.15 |
| 5 | 91 | 5 | 138 | 3H | 0.16 |
| 6 | 92 | 6 | 138 | 3H | 0.13 |
| 7 | 89 | 6 | 145 | 3H | 0.14 |
| 8 | 90 | 5 | 143 | 3H | 0.14 |
| 9 | 90 | 5 | 180 | 3H | 0.10 |
| 10 | 89 | 5 | 177 | 3H | 0.11 |
| 11 | 91 | 5 | 181 | 3H | 0.10 |

INDUSTRIAL APPLICABILITY

The polyalicyclic acrylic acid ester derivative obtained by the process of the present invention is a polymer excellent in the transparency, strength, heat resistance, water absorptivity and optical uniformity such as double refraction and thus is extremely useful as a resin for optical material for optical lenses, digital audio disks or optical memory disks.

Claims:

1. A polyacrylic acid ester derivative having repeating units represented by the formula:

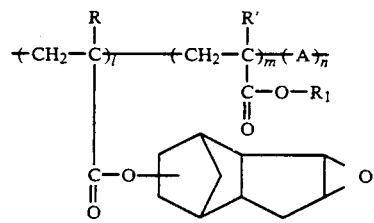

wherein R and R' independently represent a hydrogen atom or a methyl group, R$_1$ represents a C$_1$–C$_4$ linear or branched alkyl group, A represents a structural unit derived from a group copolymerizable with an acrylic acid ester, and 1, m and n are, respectively, from 0.04 to 1.0, from 0 to 0.9 and from to 0.5 in this order, provided that their sum is 1, and when m is not higher than 0.2, n is a number of not higher than 0.01 and having a molecular weight of from about 5,000 to about 1,000,000.

2. The polyacrylic acid ester derivative of claim 1, which comprises repeating units represented by the formula:

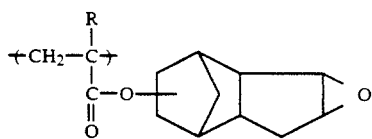

wherein R is a hydrogen atom or a methyl group, wherein l is 1 and m and n are 0.

3. The polyacrylic acid ester derivative of claim 1, which comprises repeating units represented by the formula:

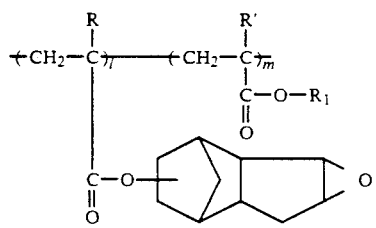

(wherein R and R' independently represent a hydrogen atom or a methyl group, and $R_1$ is a $C_1$-$C_4$ linear or branched alkyl group, wherein l is a number of from 0.05 to 0.8, m is a number of from 0.2 to 0.95, and n is 0.

4. The polyacrylic acid ester derivative of claim 1, wherein l is a number of from 0.04 to 0.8, m is a number of from 0.2 to 0.95, and n is a number of from 0.1 to 0.5.

5. The polyacrylic acid ester derivative of claim 4, wherein A is the one derived from a monomer represented by the formula:

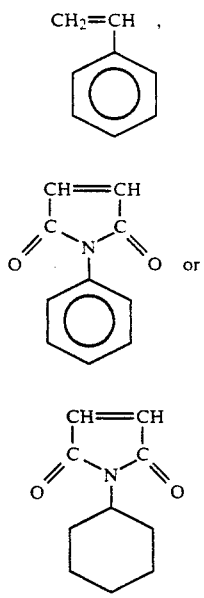

(9)

6. A process for producing a polyacrylic acid ester derivative of claim 2, which comprises radical-polymerizing a monomer represented by the formula:

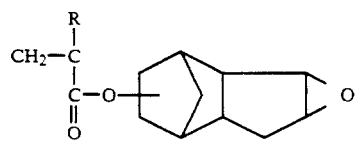

wherein R is a hydrogen atom or a methyl group.

7. A process for producing a polyacrylic acid ester derivative of claim 3, which comprises radical-copolymerizing a monomer represented by the formula:

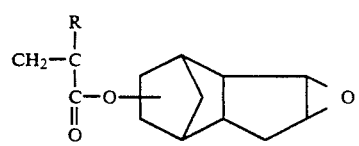

wherein R is a hydrogen atom or a methyl group and a monomer represented by the formula:

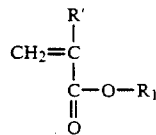

wherein R' is a hydrogen atom or a methyl group.

8. A process for producing a polyacrylic acid ester derivative of claim 4, which comprises radical-copolymerizing a monomer represented by the formula:

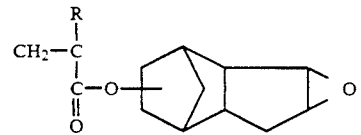

and a monomer represented by the formula:

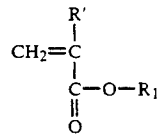

and a monomer represented by the formula:

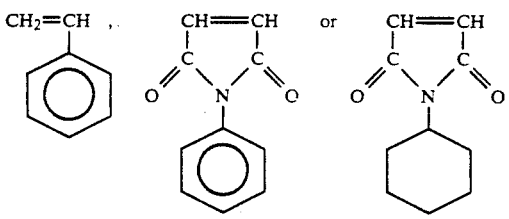

9. A resin composition for optical material comprising a polyacrylic acid ester derivative or polymer of any one of claims 1 to 5.

10. The shaped product of optical material obtained by injection-molding a resin composition comprising an acrylic acid ester derivative of any one of claim 1 to 4.

* * * * *